(12) United States Patent
Iwahashi

(10) Patent No.: US 10,420,954 B2
(45) Date of Patent: Sep. 24, 2019

(54) LIGHT EXPOSURE APPARATUS

(71) Applicant: PANASONIC INTELLECTUAL PROPERTY MANAGEMENT CO., LTD., Osaka (JP)

(72) Inventor: Tomoya Iwahashi, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 16/043,489

(22) Filed: Jul. 24, 2018

(65) Prior Publication Data
US 2019/0030360 A1    Jan. 31, 2019

(30) Foreign Application Priority Data
Jul. 28, 2017   (JP) .................... 2017-147212

(51) Int. Cl.
| | |
|---|---|
| A61N 5/06 | (2006.01) |
| F21V 7/00 | (2006.01) |
| F21S 6/00 | (2006.01) |
| F21V 7/04 | (2006.01) |
| F21S 10/02 | (2006.01) |
| F21Y 113/10 | (2016.01) |
| F21Y 105/18 | (2016.01) |
| F21Y 115/10 | (2016.01) |
| F21Y 103/33 | (2016.01) |
| F21Y 113/13 | (2016.01) |

(52) U.S. Cl.
CPC .............. *A61N 5/0618* (2013.01); *F21S 6/00* (2013.01); *F21S 10/023* (2013.01); *F21V 7/0008* (2013.01); *F21V 7/045* (2013.01); *A61N 2005/0642* (2013.01); *A61N 2005/0652* (2013.01); *A61N 2005/0663* (2013.01); *F21Y 2103/33* (2016.08); *F21Y 2105/18* (2016.08); *F21Y 2113/10* (2016.08); *F21Y 2113/13* (2016.08); *F21Y 2115/10* (2016.08)

(58) Field of Classification Search
CPC .......... A61N 5/0618; A61N 2005/0642; A61N 2005/0652; A61N 2005/0658–0663; F21S 6/00; F21S 10/023; F21V 7/045
See application file for complete search history.

(56) References Cited

U.S. PATENT DOCUMENTS

2003/0223036 A1* 12/2003 Anderson .............. A61B 3/066
351/205

FOREIGN PATENT DOCUMENTS

JP        2005-063687 A    3/2005

* cited by examiner

*Primary Examiner* — Anabel Ton
(74) *Attorney, Agent, or Firm* — Greenblum & Bernstein, P.L.C.

(57) ABSTRACT

A light exposure apparatus emits light which activates the body of the user. The light exposure apparatus includes a blue light source which emits blue light and a red light source which emits red light. The light includes blue light and red light. Blue light has a peak wavelength in a range from 445 nm to 500 nm. Red light has a peak wavelength in a range from 600 nm to 680 nm. The intensity of the peak wavelength of blue light is the strongest in the spectrum of the light, and the intensity of the peak wavelength of red light is the second strongest in the spectrum of the light. The relative intensity of the peak wavelength of the red light with respect to the peak wavelength of the blue light is in a range from 0.1 to 0.5 inclusive.

10 Claims, 6 Drawing Sheets

□ BLUE LIGHT EMITTING ELEMENT
▨ RED LIGHT EMITTING ELEMENT
▨ WHITE LIGHT EMITTING ELEMENT

FIG. 9

| | | EXAMPLE 1 | EXAMPLE 2 | EXAMPLE 3 | EXAMPLE 4 | EXAMPLE 5 | EXAMPLE 6 |
|---|---|---|---|---|---|---|---|
| OUTER CIRCUMFERENCE OF BOARD | BLUE LIGHT EMITTING ELEMENT | 32 | 32 | 32 | 0 | 32 | 32 |
| | WHITE LIGHT EMITTING ELEMENT | 0 | 0 | 0 | 32 | 0 | 0 |
| INNER CIRCUMFERENCE OF BOARD | BLUE LIGHT EMITTING ELEMENT | 16 | 8 | 0 | 12 | 8 | 0 |
| | RED LIGHT EMITTING ELEMENT | 8 | 16 | 24 | 8 | 8 | 8 |
| | GREEN LIGHT EMITTING ELEMENT | 8 | 8 | 8 | 8 | 8 | 8 |
| | WHITE LIGHT EMITTING ELEMENT | 0 | 0 | 0 | 4 | 8 | 16 |
| CHROMATICITY COORDINATE X | | 0.19 | 0.25 | 0.31 | 0.31 | 0.21 | 0.24 |
| CHROMATICITY COORDINATE Y | | 0.11 | 0.14 | 0.17 | 0.29 | 0.15 | 0.19 |

LIGHT EXPOSURE APPARATUS

CROSS REFERENCE TO RELATED APPLICATION

This application claims the benefit of priority of Japanese Patent Application Number 2017-147212 filed on Jul. 28, 2017, the entire content of which is hereby incorporated by reference.

BACKGROUND

1. Technical Field

The present disclosure relates to a light exposure apparatus capable of improving the appearance of a user irradiated with light.

2. Description of the Related Art

Conventionally, patent literature 1 (Japanese Unexamined Patent Application Publication No. 2005-63687) discloses a light emitting apparatus including a first phosphor which emits blue light and a second phosphor which emits blue light having an emission peak wavelength different from that of the first phosphor. The light emitting apparatus is capable of adjusting a biological rhythm by emitting blue light toward a user.

SUMMARY

However, the face etc. of a user irradiated with blue light emitted by such a light exposure apparatus inevitably looks pale. Such user's face looks unnatural and unusual to other persons.

In view of this, the present disclosure has an object to provide a light exposure apparatus capable of improving the appearance of a user irradiated with light emitted by a light exposure apparatus according to the present disclosure.

In order to achieve the above object, the light exposure apparatus according to an aspect of the present disclosure is a light exposure apparatus which emits light that activates a body of a user includes a blue light source which emits blue light and a red light source which emits red light. The emission light includes the blue light and the red light. The blue light has a peak wavelength in a wavelength range from 445 nm to 500 nm. The red light has a peak wavelength in a wavelength range from 600 nm to 680 nm. The intensity of the emission light is strongest at the peak wavelength of the blue light in a spectrum of the emission light, and the intensity of the emission light is second strongest at the peak wavelength of the red light in the spectrum. The intensity of the emission light at the peak wavelength of the red light relative to the intensity at the peak wavelength of the blue light ranges from 0.1 to 0.5.

According to the present disclosure, it is possible to improve the appearance of the user irradiated with light emitted by the light exposure apparatus.

BRIEF DESCRIPTION OF DRAWINGS

The figures depict one or more implementations in accordance with the present teaching, by way of examples only, not by way of limitations. In the figures, like reference numerals refer to the same or similar elements.

FIG. 9 is a diagram indicating the numbers of blue, red, white, and green light sources of the light exposure apparatus and chromaticity coordinates.

DETAILED DESCRIPTION OF THE EMBODIMENTS

Outline

Figure 1:
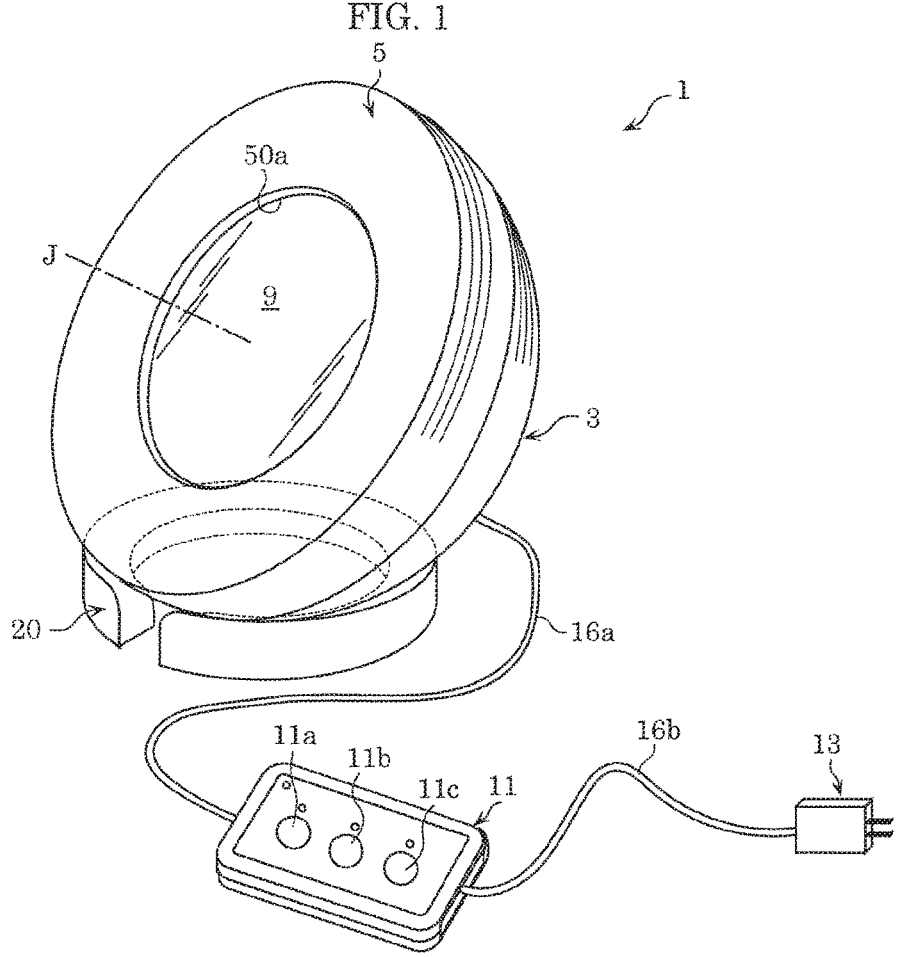
FIG. 1 is a perspective view of a light exposure apparatus according to Embodiment 1.

It is generally known that light having a predetermined wavelength when entering the eyes of a person activates the body of the person. Light which activates the body includes blue light. It is known that blue light provides an advantageous effect of improving a biological rhythm of the person exposed to light including the blue light for a certain period of time or longer time. Here, the biological rhythm is a rhythm that exhibits a cycle of one day, such as when a person, as a physiological phenomenon, naturally feels sleepy at a certain time and naturally wakes up after sleeping for a certain time. It is known that blue light when applied to a person from morning to around p.m. 3 o'clock provides an advantageous effect of increasing the generation amount of a hormone called melatonin, serotonin, and the like in the body of the person. For this reason, it is advantageous that blue light enters both the eyes of the person simultaneously so as to activate the body of the person.

It is also known that light having a peak wavelength in a range from 465 nm to 490 nm affects the biological hormones most due to sensitivity of human eyes (the sensitivity is also referred to as a biological effect level or a biological stimulation level). For this reason, it is advantageous that light to be applied to human eyes include a large amount of light having a wavelength in a range from 465 nm to 490 nm.

Through daily exposure to such light, the amount of secretion of a hormone called serotonin increases. The increased amount of serotonin provides sustenance and increases the amount of secretion of a hormone called melatonin at night. The increased amount of melatonin provides the person with a sound sleep. As a result, the person can adjust the biological rhythm.

Hereinafter, the embodiment of the present disclosure is described with reference to the drawings. The embodiment described below illustrates one specific example of the present disclosure. Thus, the numerical values, shapes, materials, constituent elements, the arrangement and connection of the constituent elements described in the following embodiment are mere examples and not intended to limit the present disclosure. Accordingly, among the constituent elements in the following embodiment, the constituent elements that are not recited in any independent claim that defines the most generic concept of the present disclosure are described as arbitrary constituent elements.

In addition, the phrase "approximately . . . " is used, in an exemplary case of "approximately the same one", to include not only "the same one" but also "substantially the same one".

Incidentally, each of the diagrams is a schematic view and not necessarily illustrated in a strict manner. Furthermore, in each of the diagrams, substantially the same elements are assigned the same reference signs, and the redundant descriptions of such elements are omitted or simplified.

Hereinafter, a light exposure apparatus according to Embodiment 1 is described.

Embodiment 1

[Configuration]

First, the configuration of light exposure apparatus 1 according to this embodiment is described with reference to FIGS. 1 to 3.

FIG. 1 is a perspective view of light exposure apparatus 1 according to Embodiment 1. FIG. 2 is a perspective view of light exposure apparatus 1 according to Embodiment 1. FIG. 3 is a plan view of light emitting module 7 of light exposure apparatus 1 according to Embodiment 1.

Figure 2:
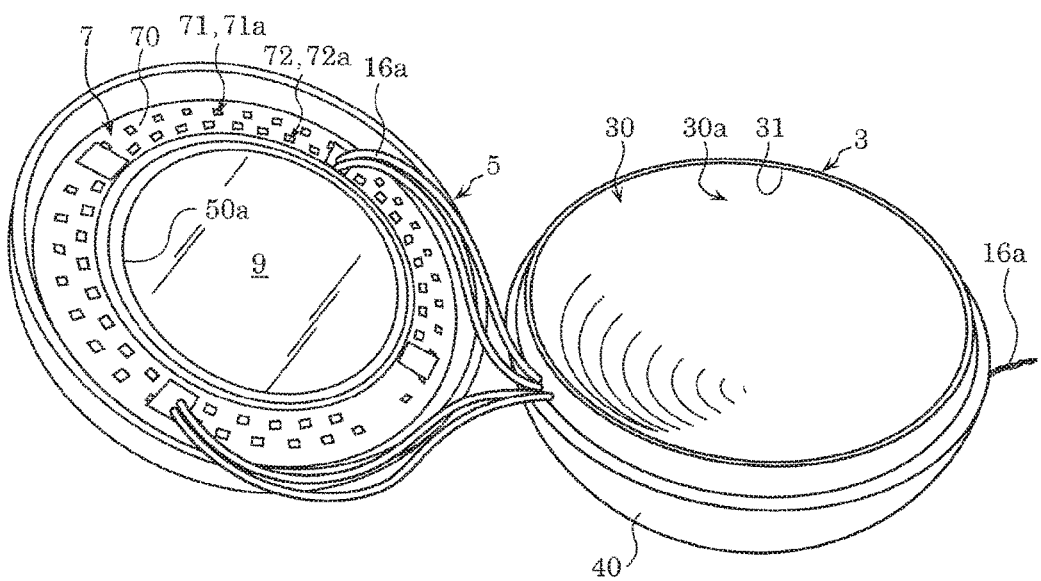
FIG. 2 is a perspective view of the light exposure apparatus according to Embodiment 1.

As illustrated in FIGS. 1 and 2, light exposure apparatus 1 is an apparatus capable of emitting light which activates a body of a user so as to adjust a biological rhythm of the user exposed to the emitted light. Light which activates the body is blue light. For example, the user can place light exposure apparatus 1 on a desk, a shelve, a dresser or the like in an office, a home, etc and can be exposed to light which activates the body emitted from light exposure apparatus 1. In this embodiment, light which is emitted from light exposure apparatus 1 includes blue light and red light.

It is to be noted that "blue" of blue light here does not mean blue in a strict sense, and blue light means light which normally looks blue. Blue light in this embodiment is, for example, light having a wavelength ranging from 445 nm to 500 nm.

Light exposure apparatus 1 includes case 3, frame body 5, light emitting module 7, light distribution panel 9, operation unit 11, adaptor 13, and base 20.

Case 3 is approximately hemispherical and has first opening portion 31 at the front side thereof. Light exposure apparatus 1 emits light from the front side. Case 3 has inner surface 30a formed therein to be approximately hemispherical. Case 3 has inner shell portion 30 and outer shell portion 40. Inner shell portion 30 and outer shell portion 40 are each approximately hemispherical and has an opening at the front side thereof. Case 3 has a double-structure body composed of inner shell portion 30 and outer shell portion 40. First opening portion 31 has inner surface 30a formed therein to be approximately hemispherical. Light reflected by inner surface 30a exits through first opening portion 31.

Case 3 is made of a white resin material etc. such as acryl and polycarbonate. Inner surface 30a of case 3 is inner surface 30a of inner shell portion 30, and is configured as a reflection surface that reflects light toward second opening portion 50a. Inner surface 30a of case 3 is coated with white coating material which reflects light. In this embodiment, high-cast 3155CA (white toner of 3%) is used for case 3. It is to be noted that the material for inner surface 30a of case 3 is not limited to a white resin, and inner surface 30a can be made of metal. Inner surface 30a of case 3 may be covered by a metal reflective film.

Frame body 5 has a flat annular shape and is detachably attached to first opening portion 31 of case 3. Frame body 5 has second opening portion 50a formed therein. Light such as blue light, red light etc. reflected by inner surface 30a exits through second opening portion 50a.

Light emitting module 7 has a flat annular shape and is disposed on a surface of frame body 5. The surface faces case 3 when used. In other words, light emitting module 7 is oriented in frame body 5 to emit emission light toward inner surface 30a of case 3. In a front plan view of light exposure apparatus 1, light emitting module 7 is overlapped with frame body 5. More specifically, light emitting module 7 is disposed in frame body 5 in such a manner that the center axis of light emitting module 7 and the center axis of frame body 5 approximately match with each other. In this embodiment, light emitting module 7 includes two arc-shaped boards 70, and blue light sources 71 and red light sources 72 mounted on arc-shaped boards 70.

Boards 70 are fixed to frame body 5 approximately along the periphery of frame body 5. Boards 70 are electrically connected to operation unit 11 via wiring member 16a such as a lead wire etc. for supplying power to blue light sources 71 and red light sources 72. Boards 70 may be thermally connected to a radiator unit which releases heat generated by blue light source 71 and red light source 72.

Figure 3:
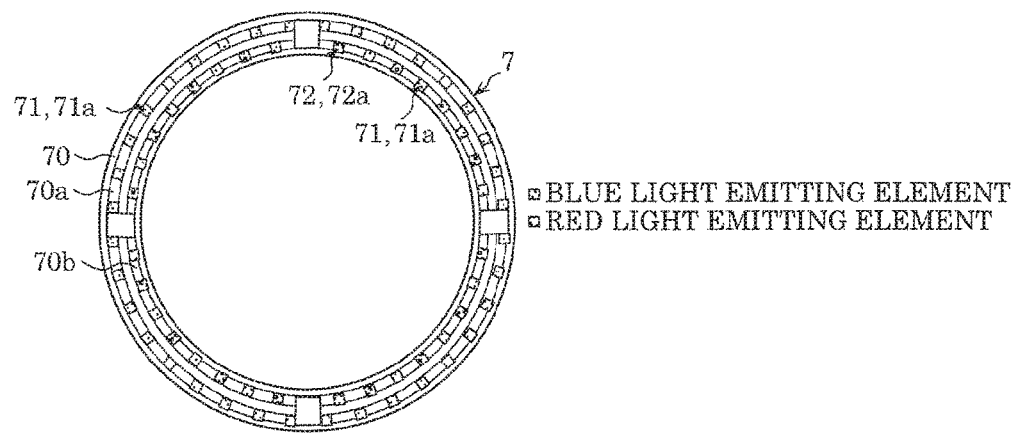
FIG. 3 is a plan view of a light emitting module of the light exposure apparatus according to Embodiment 1.

As illustrated in FIG. 3, blue light source 71 includes a plurality of blue light emitting elements 71a. In addition, red light source 72 includes a plurality of red light emitting elements 72a. The plurality of blue light emitting elements 71a and the plurality of red light emitting elements 72a are arranged annularly along the ring shape of board 70. More specifically, blue light emitting elements 71a are arranged at equal intervals along outer circumference 70a of board 70, and blue light emitting elements 71a and red light emitting elements 72a are arranged at equal intervals along inner circumference 70b of board 70. In other words, in light emitting module 7, blue light source 71 and red light source 72 are mounted to have a double ring shape in which inner circumference 70b and outer circumference 70a are included. Although blue light source 71 and red light source 72 are mounted to have the double ring shape, it is to be noted that blue light source 71 and red light source 72 may be mounted to have a single or triple ring shape.

As illustrated in FIGS. 1 and 2, blue light source 71 and red light source 72 emit light in the depth direction in light exposure apparatus 1. The depth direction is opposite to the direction in which light is emitted from light exposure apparatus 1. Blue light source 71 emits blue light toward inner surface 30a of case 3. Blue light has a peak wavelength in a range from 445 nm to 500 nm. In this embodiment, the peak wavelength of blue light is in the proximity of 465 nm. The intensity of the emission light is strongest at the peak wavelength of blue light in the spectrum of the emission light. Red light source 72 emits red light toward inner surface 30a of case 3. Red light has a peak wavelength in a range from 600 nm to 680 nm. In this embodiment, the peak wavelength of red light is in the proximity of 635 nm. The intensity of the emission light is second strongest at the peak wavelength of red light in the spectrum.

In addition, the peak wavelength of blue light that is emitted by blue light source 71 in light exposure apparatus 1 according to this embodiment is in the proximity of 465 nm, a general blue light source can be employed. For this reason, it is possible to activate the body of the user without using any custom-made blue light source. Therefore, light exposure apparatus 1 can be manufactured at a lower manufacturing cost.

Blue light emitting elements 71a and red light emitting elements 72a are LED elements called surface mount devices (SMDs). Specifically, an SMD-type LED element is a package-type LED element in which an LED chip (light emitting element) is mounted in a cavity and is sealed by a phosphor-containing resin in the cavity. Turned on and off control for blue light source 71 and red light source 72 is performed by a not-shown control circuit provided in operation unit 11. Furthermore, dimming and toning control for blue light source 71 and red light source 72 is performed by the control circuit provided in operation unit 11. Blue light emitting elements 71a and red light emitting elements 72a are LED chips.

It is to be noted that the configuration of blue light emitting elements 71a and red light emitting elements 72a is not limited to the above configuration, and that a following chip on board (COB) type module may be used: the COB module having blue light emitting element 71a and red light emitting element 72a which are LED chips directly mounted on boards 70. In addition, blue light emitting elements 71a of blue light source 71 and red light emitting elements 72a of red light source 72 are not limited to LEDs, and may be, for example, other solid-state light emitting elements including semiconductor light emitting elements such as semiconductor lasers etc, organic or inorganic electro luminescent (EL) elements etc.

Light distribution panel 9 is fixed to the surface of frame body 5 (the surface faces case 3 when used), and covers second opening portion 50a of frame body 5. Light distribution panel 9 has a light distribution control function for increasing directivity in the front surface direction of light exposure apparatus 1 and reducing light dispersion in the direction orthogonal to optical axis J of light exposure apparatus 1. The light dispersion in the direction orthogonal to optical axis J is reduced significantly when light distribution panel 9 is disposed in second opening portion 50a of frame body 5, than when no light distribution panel 9 is disposed at second opening portion 50a of frame body 5. Light distribution panel 9 may be configured by attaching a light distribution film having a light distribution control function to a light transmissive panel, or by providing light distribution panel 9 with a fine uneven surface as a front or back surface. In this embodiment, a light distribution film made by 3M Japan is used for light distribution panel 9.

Operation unit 11 is formed as one of a switch and an input unit for controlling light emission states of light emitting module 7. Operation unit 11 is electrically connected to light emitting module 7 via wiring member 16a, and is electrically connected to adaptor 13 via other wiring member 16b. A power source lamp turns on in operation unit 11 upon receiving supply of electric power from outside. Operation unit 11 includes three buttons of 11a, 11b, and 11c, and is capable of adjusting the intensity of blue light included in emission light that is emitted by light exposure apparatus 1. More specifically, pressing first button 11a enables Y-minute emission of blue light having an intensity of X included in the emission light, pressing second button 11b enables 2×Y-minute emission of blue light having an intensity of X/2 included in the emission light, and pressing third button 11c enables 3×Y-minute emission of blue light having an intensity of X/3 included in the emission light. It is to be noted that irradiation time does not always need to be in units of minutes, and may be in units of seconds or hours.

Adaptor 13 is AC-DC adaptor 13 that is connected to an outlet through which electric power can be supplied from outside. Adaptor 13 converts alternating power that is supplied from an external device such as a commercial-use power supply to direct power.

Base 20 is approximately annular with a cutout and on which case 3 can be mounted. Base 20 holds case 3. It is to be noted that base 20 when base 20 is mere a platform for case 3 is not an essential element of light exposure apparatus 1. In addition, base 20 may be configured integrally with operation unit 11. More specifically, base 20 may be provided with the plurality of buttons 11a, 11b, and 11c of operation unit 11. In other words, base 20 may also function as operation unit 11. In addition, frame body 5 may include operation unit 11. In other words, part of frame body 5 may be operation unit 11.

In light exposure apparatus as such, light that is emitted by light emitting module 7 enters and reflected by inner surface 30a of case 3 toward second opening portion 50a of frame body 5. The light reflected by inner surface 30a enters the front surface of light distribution panel 9 which covers second opening portion 50a, and passes through light distribution panel 9. Light distribution panel 9 controls the light distribution of the light. The light having the controlled light distribution is output from the front surface of light distribution panel 9. In this way, the light having an improved directivity in the front surface direction is output from light distribution panel 9. The front surface direction is the direction in which light exposure apparatus 1 emits light, and thus is a forward direction.

Next, the spectra of light emitted from light exposure apparatus 1 according to this embodiment is described with reference to FIG. 4.

Figure 4:
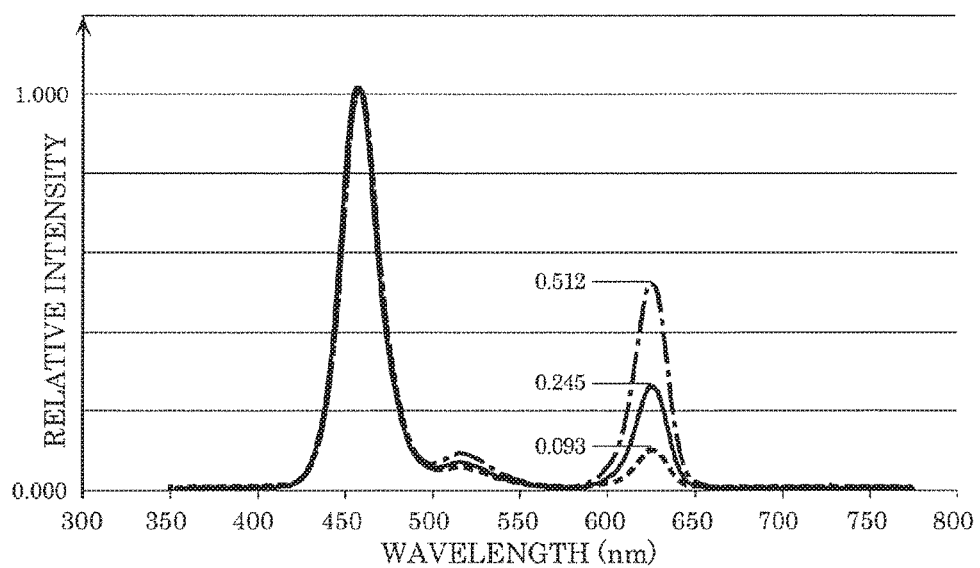
FIG. 4 is a diagram indicating spectra of light emitted from the light exposure apparatus according to Embodiment 1.

FIG. 4 is a diagram indicating the spectra of the light emitted from light exposure apparatus 1 according to Embodiment 1.

As illustrated in the graph of FIG. 4, a broken line indicates a spectrum of light emitted from light exposure apparatus 1 in Experiment 1, an alternate long and short dash line indicates a spectrum of light emitted from light exposure apparatus 1 in Experiment 2, and a solid line indicates a spectrum of light emitted from light exposure apparatus 1 in this embodiment.

In the spectrum of the light emitted from light exposure apparatus 1 in Experiment 1, the peak wavelength has an intensity of 0.093 in a wavelength range from 600 nm to 680 nm relative to the peak wavelength of blue light. In this case, the face of a user of light exposure apparatus 1 looks pale. Such user's face looks unnatural and unusual to other persons.

In the spectrum of the light emitted from light exposure apparatus 1 in Experiment 2, the peak wavelength has an intensity of 0.512 in a wavelength range from 600 nm to 680 nm relative to the peak wavelength of blue light. In this case, the face of a user of light exposure apparatus 1 looks somewhat flushed. Such user's face looks unnatural and unusual to other persons.

In the spectrum of light emitted from light exposure apparatus 1 in this embodiment, the peak wavelength has an intensity of 0.245 in a wavelength range from 600 nm to 680 nm relative to the intensity at the peak wavelength of blue light. In this case, the face of the user of light exposure apparatus 1 does not look pale or flushed. Thus, the user's face looks natural and not unusual to other persons.

For this reason, the red light included in the light that is emitted from light exposure apparatus 1 is designed such that the peak wavelength of the red light has an intensity in a range from 0.1 to 0.5 relative to the peak wavelength of the blue light included in the light. In particular, the relative intensity of the peak wavelength in the red-light wavelength range from 600 nm to 680 nm is desirably in a range from 0.2 to 0.3.

Next, glare felt by neighbour H2 of user H1 when light exposure apparatus 1 according to this embodiment is actually used is described with reference to FIGS. 5 and 6.

Figure 5:
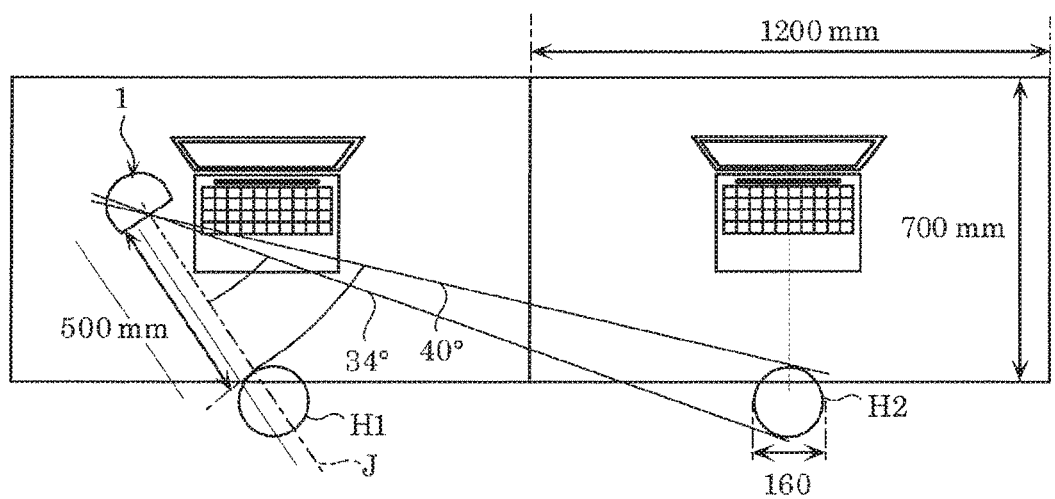
FIG. 5 is a diagram indicating the relationship between the user and a neighbour adjacent to the user when the light exposure apparatus according to Embodiment 1 is disposed on a desk of the user.

FIG. 5 is a diagram indicating the relationship between user H1 and neighbour H2 adjacent to user H1 when light exposure apparatus 1 according to Embodiment 1 is disposed on a desk of user H1. FIG. 6 is a diagram indicating light distribution characteristics of light exposure apparatus 1 according to Embodiment 1.

First, as illustrated in FIG. 5, it is assumed that user H1 is present on optical axis J of light exposure apparatus 1, the distance from light exposure apparatus 1 to user H1 is 50 cm, and the distance from neighbour H2 present in the direction orthogonal to optical axis J to user H1 is 120 cm. In this case, it is assumed that neighbour H2 is present in a range in which an angle of a virtual line that connects light exposure apparatus 1 and neighbour H2 with respect to optical axis J is approximately from 34 degrees to 40 degrees. In other words, it is assumed that the light from light exposure apparatus 1 enters neighbour H2 in the range approximately from 34 degrees to 40 degrees.

Figure 6:
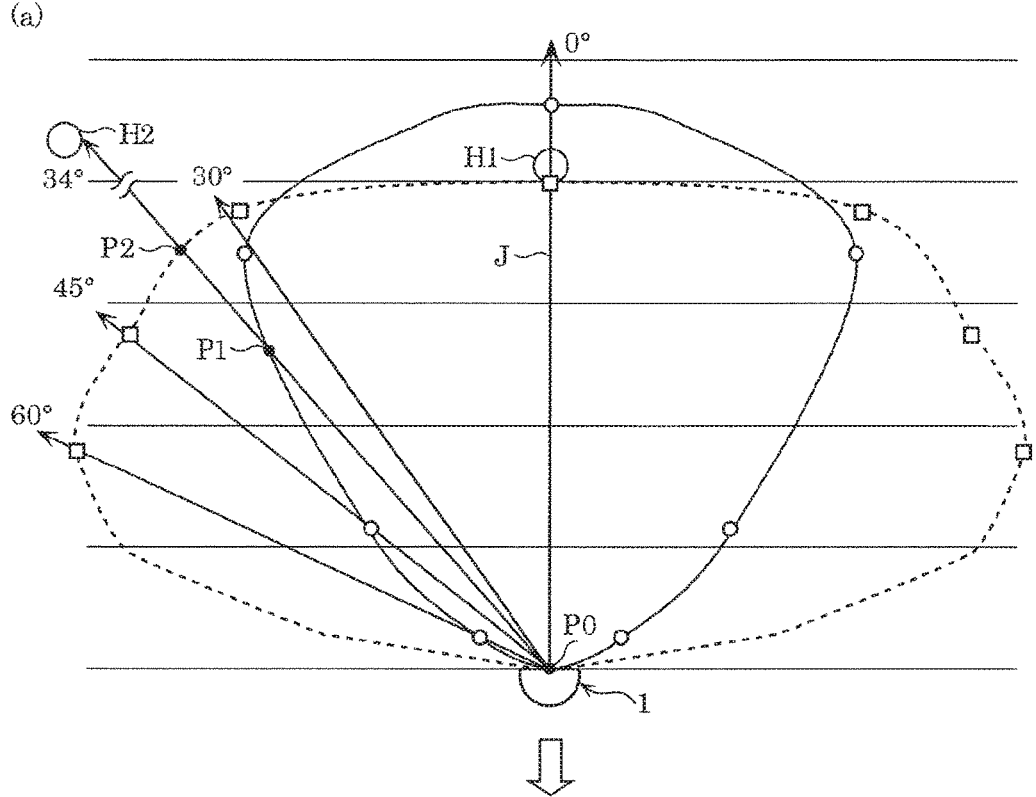
FIG. 6 is a diagram indicating light distribution characteristics of the light exposure apparatus according to Embodiment 1.
Figure 6:
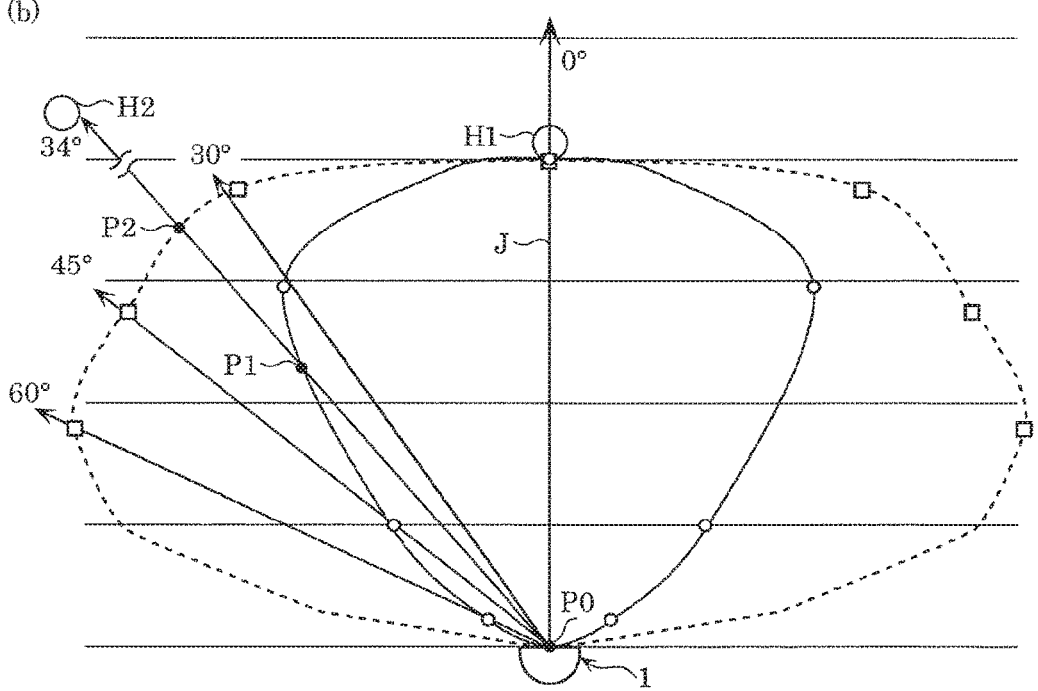

As illustrated in (a) of FIG. 6, a broken line is a light distribution curve indicating a case in which no light distribution panel 9 is provided in second opening portion 50a, and a solid line is a light distribution curve indicating a case in which light distribution panel 9 is provided in second opening portion 50a. By providing light distribution panel 9 in second opening portion 50a, light dispersion in the direction orthogonal to optical axis J is reduced, which increases directivity in the optical axis J direction that is the front surface direction. The optical axis J direction is the direction in which the light is emitted from light exposure apparatus 1.

The directivity in the front surface direction is increased significantly when light distribution panel 9 is provided in second opening portion 50a than in no light distribution panel 9 is provided in second opening portion 50a. For this reason, as indicated by a solid line in (b) of FIG. 6, input electric power to be supplied to light emitting module 7 is reduced when light distribution panel 9 is provided in second opening portion 50a. In this case, in this embodiment, input electric power is reduced by 17% in the optical axis J direction by reducing the input electric power to be supplied to light emitting module 7 such that the light distribution curve in the case where light distribution panel 9 is provided in second opening portion 50a and the light distribution curve in the case where no light distribution panel 9 is provided in second opening portion 50a match on optical axis J. In this embodiment, irradiation power of blue light to be emitted from blue light source 71 is in a range from 4.5 W to 9.9 W.

It is assumed that the position of light exposure apparatus 1 is P0, the point at which a solid line and the virtual line that connects the position of neighbour H2 and the position of light exposure apparatus 1 is P1, and the point at which a broken line and the virtual line that connects the position of neighbour H2 and the position of light exposure apparatus 1 is P2. It is assumed that the length between P0 and P1 is a first length, the length between P0 and P2 is a second length, and the ratio between the first length and the second length is approximately 4:6. In other words, the brightness of light to be emitted to neighbour H2 is reduced by approximately 33% when light distribution panel 9 is provided in second opening portion 50a, compared to the case where no light distribution panel 9 is provided in second opening portion 50a. For this reason, the brightness of light to be emitted to neighbour H2 is reduced by 30% or higher when light distribution panel 9 is provided in second opening portion 50a compared to the case where no light distribution panel 9 is provided in second opening portion 50a.

In view of the above, light distribution panel 9 according to this embodiment has a property of reducing brightness by 30% or higher in the direction ranging from 34 degrees to 40 degrees with respect to optical axis J of light exposure apparatus 1 when light distribution panel 9 is provided in second opening portion 50a compared to the case where no light distribution panel 9 is provided in second opening portion 50a, compared to the case where no light distribution panel 9 is provided in second opening portion 50a. In other words, when neighbour H2 looks light exposure apparatus 1, neighbour H2 can feel that the brightness is reduced.

Advantageous Effects

Next, advantageous effects provided by light exposure apparatus 1 according to this embodiment are described.

As described above, light exposure apparatus 1 according to this embodiment emits light which activates the body of the user. Light exposure apparatus 1 includes blue light source 71 which emits blue light and red light source 72 which emits red light. The light includes blue light and red light. Blue light has a peak wavelength in a range from 445 nm to 500 nm. Red light has a peak wavelength in a range from 600 nm to 680 nm. The intensity of the emission light is strongest at the peak wavelength of the blue light in the spectrum of the emission light, and the intensity at the peak wavelength of the red light is second strongest in the spectrum. The intensity at the peak wavelength of the red light relative to the intensity at the peak wavelength of the blue light is in a range from 0.1 to 0.5.

In view of this, the blue light has a peak wavelength in the range from 445 nm to 500 nm, and the red light has a peak wavelength in the range from 600 nm to 680 nm. Assuming that the intensity at the peak wavelength of the blue light in the spectrum is 1, the intensity at the peak wavelength of the red light is in a range from 0.1 to 0.5. The use of mixed light of the blue light and the red light prevents the user's face looks pale or somewhat flushed. Thus, even when other persons look the user using light exposure apparatus 1, the user looks natural to the other persons.

Accordingly, it is possible to improve the appearance of the user irradiated with light emitted from light exposure apparatus 1.

In light exposure apparatus 1 according to this embodiment, blue light source 71 includes a plurality of blue light emitting elements 71a, and red light source 72 includes a plurality of red light emitting elements 72a. Light exposure apparatus 1 further includes: light emitting module 7 having board 70 which has a ring shape and on which blue light source 71 and red light source 72 are mounted; case 3 having inner surface 30a that is approximately hemispherical and reflects emission light, and having first opening portion 31 through which the light reflected by inner surface 30a exits; and frame body 5 attached to first opening portion 31 and having second opening portion 50a though which the light reflected by inner surface 30a passes. In other words, light emitting module 7 is oriented in frame body 5 to emit the emission light toward inner surface 30a of case 3.

In this way, light emitting module 7 includes annular board 70, the plurality of blue light emitting elements 71a and the plurality of red light emitting elements 72a arranged annularly on annular board 70. Blue light source 71 and red light source 72 are arranged on frame body 5 to emit the emission light toward inner surface 30a having an annular shape of case 3. In this way, the light including the blue light and the red light is reflected by inner surface 30a of case 3 and passes through second opening portion 50a. For this reason, it is possible to increase the directivity in the front surface direction in light exposure apparatus 1.

Light exposure apparatus 1 according to this embodiment further includes light distribution panel 9 which covers second opening portion 50a, and passes through and distributes the emission light.

In this way, light distribution panel 9 controls distribution of the light including the blue light and the red light which pass through second opening portion 50a. For this reason, the directivity of the light in the front surface direction of light exposure apparatus 1 is increased, and dispersion of the light in the direction orthogonal to light exposure apparatus 1 can be reduced. For this reason, for example, even when a user uses light exposure apparatus 1 in an environment such as an office or the like, a neighbour is unlikely to be dazzled by the light from light exposure apparatus 1.

In addition, by providing light distribution panel 9 in second opening portion 50a, it is possible to reduce input electric power to light emitting module 7, which can reduce the running cost of light exposure apparatus 1.

In addition, light exposure apparatus 1 according to this embodiment, light distribution panel 9 has a property of reducing brightness by 30% or higher in the direction ranging from 34 degrees to 40 degrees with respect to optical axis J of light exposure apparatus 1 when light distribution panel 9 is provided in second opening portion 50a, compared to the case where no light distribution panel 9 is provided in second opening portion 50a.

In this way, light distribution panel 9 covers second opening portion 50a, and controls distribution of the light including the blue light, the red light, and the white light which pass through second opening portion 50a. Light distribution panel 9 reduces brightness by 30% or higher in the direction ranging from 34 degrees to 40 degrees with respect to optical axis J of light exposure apparatus 1 when light distribution panel 9 is provided in second opening portion 50a of frame body 5, compared to the case where no light distribution panel 9 is provided in frame body 5. For this reason, the directivity of light in the front surface direction of light exposure apparatus 1 is increased, and dispersion of light in the direction orthogonal to light exposure apparatus 1 can be reduced. For this reason, for example, even when the user uses light exposure apparatus 1 in the environment such as the office or the like, the neighbour is unlikely to be dazzled by the light from light exposure apparatus 1.

In addition, by providing light distribution panel 9 in second opening portion 50a, it is possible to reduce input electric power to light emitting module 7, which can reduce the running cost of light exposure apparatus 1.

In addition, in light exposure apparatus 1 according to this embodiment, the plurality of blue light emitting elements 71a and the plurality of red light emitting elements 72a are arranged annularly along the ring shape of annular board 70. The plurality of blue light emitting elements 71a are arranged along the outer circumference of annular board 70. The plurality of red light emitting elements 72a are arranged along the inner circumference of annular board 70.

In light exposure apparatus 1 according to this embodiment, the plurality of blue light emitting elements 71a are arranged in addition to the plurality of red light emitting elements 72a such that the plurality of blue light emitting elements 71a and the plurality of red light emitting elements 72a are alternately arranged along the inner circumference of board 70 in units of a predetermined number of light emitting elements.

The intensity at the peak wavelength of the red light relative to the intensity at the peak wavelength of the blue light is in a range from 0.2 to 0.3.

Embodiment 2

[Configuration]

The configuration of a light exposure apparatus according to this embodiment is described.

Figure 7:
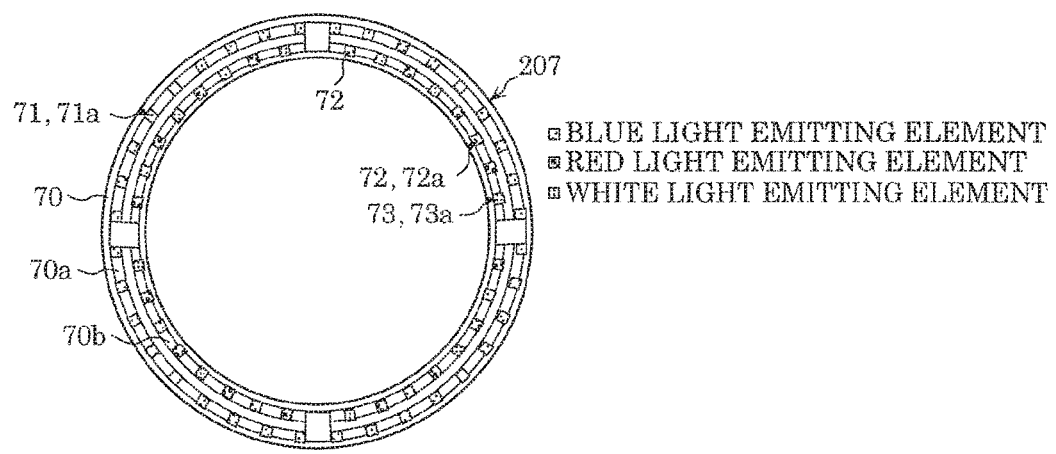
FIG. 7 is a plan view of a light emitting module of a light exposure apparatus according to Embodiment 2.

FIG. 7 is a plan view of light emitting module 207 of the light exposure apparatus according to Embodiment 2.

In this embodiment, light emitting module 207 has white light source 73, which is a difference from Embodiment 1. The light exposure apparatus according to this embodiment is the same as that of Embodiment 1 unless otherwise specified. The same elements are assigned the same reference signs, and are not described in detail again.

As illustrated in FIG. 7, light emitting module 207 includes white light source 73 which emits white light. White light source 73 includes a plurality of white light emitting elements 73a. Blue light emitting elements 71a, red light emitting elements 72a, and white light emitting elements 73a are arranged at equal intervals along the inner circumference of board 70. In other words, in light emitting module 207, blue light source 71, red light source 72, and white light source 73 are mounted so as to form double rings along inner circumference 70b and outer circumference 70a.

White light emitting elements 73a may be either SMD-type elements, COB-type elements, or other solid-state light emitting elements including semiconductor light emitting elements such as semiconductor lasers etc, organic or inorganic electro luminescent (EL) elements etc.

In this embodiment, light which activates the body of a user is blue light and white light. White light provides an effect of activating a brain wave of the user exposed to light including the white light for a certain period of time or longer time. "White" in white light here does not mean white in a strict sense, and white light means light which normally looks white. White light is, for example, mixed light of visible light rays having different colors (such as blue light, green light, red light etc.)

Next, the spectrum of the light exposure apparatus according to this embodiment is described with reference to FIG. 8.

Figure 8:
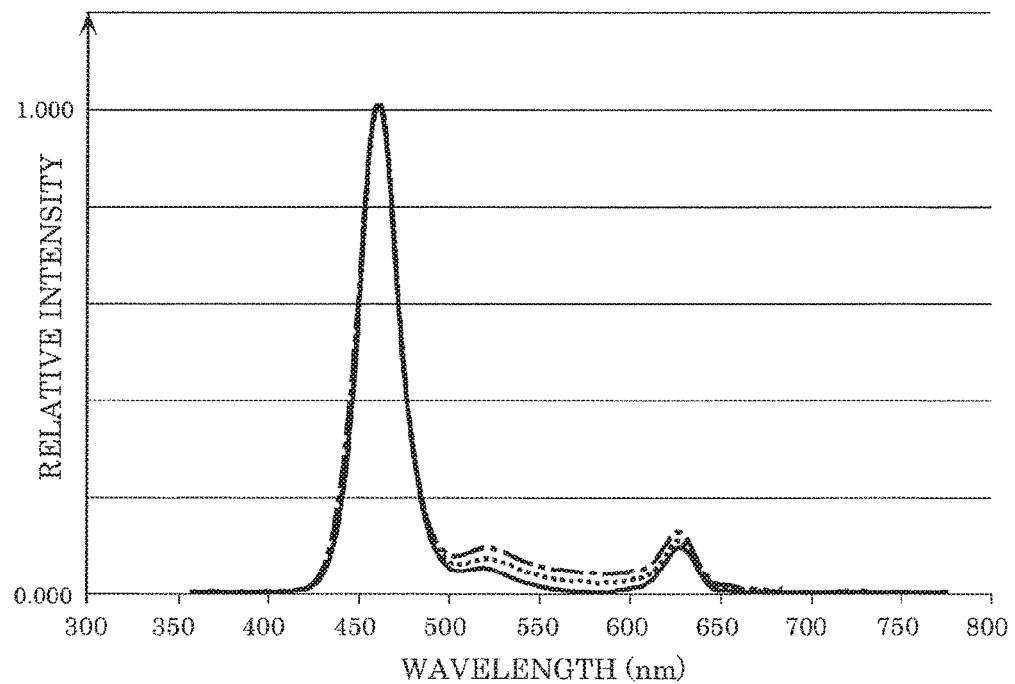
FIG. 8 is a diagram indicating a spectrum of the light exposure apparatus according to Embodiment 2.

FIG. 8 is a diagram indicating a spectrum of the light exposure apparatus according to Embodiment 2.

As illustrated in the graph of FIG. 8, a solid line indicates a spectrum of light emitted from the light exposure apparatus in Experiment Example 1, a broken line indicates a spectrum of light emitted from the light exposure apparatus in Experiment Example 2, and an alternate long and short dash line indicates a spectrum of light emitted from the light exposure apparatus in Experiment Example 3.

The light exposure apparatus in Experiment Example 1 emits light having a smaller intensity in a light wavelength range from 500 nm to 630 nm relative to the light emitted by the light exposure apparatuses in Experiment Examples 2 and 3. In particular, in the light exposure apparatus in Experiment Example 1, a minimum intensity of the emission light in a wavelength range from 550 nm to 600 nm in the spectrum relative to the intensity at the peak wavelength of the blue light is approximately 0. In other words, light such as yellow and yellow green light is almost never emitted from the light exposure apparatus in Experiment 1. For this reason, in the light exposure apparatus in Experiment Example 1, for example, the color of the closing worn by a user looks different, which looks unnatural to other persons.

In comparison, the light exposure apparatuses in Experiment Examples 2 and 3, a minimum intensity of the emission light in a wavelength range from 550 nm to 600 nm in the spectrum relative to the intensity at the peak wavelength of the blue light is 0.03 or higher, and the peak wavelength of the blue light is smaller than the peak wavelength of the red light in the spectrum. For this reason, in the light exposure apparatus in Experiment Example 1, the color of the closing worn by a user looks the same as the actual color, which looks natural to other persons. It is to be noted that a minimum intensity of the emission light in a wavelength range from 550 nm to 600 nm in the spectrum relative to the intensity at the peak wavelength of the blue light is preferably 0.05 or higher.

Advantageous Effects

Next, advantageous effects provided by the light exposure apparatus according to this embodiment are described.

As described above, the light exposure apparatus according to this embodiment further include white light source 73 which emits white light. The light further includes white light. A minimum intensity of the emission light in a wavelength range from 550 nm to 600 nm in the spectrum relative to the intensity at the peak wavelength of the blue light is 0.03 or higher.

In this way, a minimum intensity of the white light in a wavelength range from 550 nm to 600 nm in the spectrum relative to the intensity at the peak wavelength of the blue light is 0.03 or higher. For this reason, it is possible to prevent the color of the closing worn by the user from looking different under the white light. Thus, it is possible to further improve the appearance of the user irradiated with light.

In the light exposure apparatus according to this embodiment, blue light source 71 includes a plurality of blue light emitting elements 71a, and red light source 72 includes a plurality of red light emitting elements 72a. White light source 73 includes a plurality of white light emitting elements 73a. The light exposure apparatus further includes: light emitting module 207 having board 70 which has a ring shape and on which blue light source 71, red light source 72, and white light source 73 are mounted; case 3 having inner surface 30a that is approximately hemispherical and reflects emission light, and having first opening portion 31 through which the emission light reflected by inner surface 30a exits; and frame body 5 attached to first opening portion 31 and having second opening portion 50a though which the emission light reflected by inner surface 30a passes. In other words, light emitting module 7 is oriented in frame body 5 to emit the emission light toward the inner surface of case 3.

In addition, in the light exposure apparatus according to this embodiment, the plurality of blue light emitting elements 71a, the plurality of red light emitting elements 72a, and the plurality of white light emitting elements 73a are arranged annularly along the ring shape of annular board 70. The plurality of blue light emitting elements 71a are arranged along the outer circumference of annular board 70. The plurality of red light emitting elements 72a are arranged along the inner circumference of annular board 70. The plurality of white light emitting elements 73a are arranged along the inner circumference of annular board 70.

As for the other advantageous effects according to this embodiment, this embodiment provides the same advantageous effects as provided in Embodiment 1.

Variations

Although the present disclosure has been provided based on Embodiments 1 and 2, the present disclosure is not limited to the above Embodiments 1 and 2.

For example, since the distance between a user and a neighbour changes depending on an environment, the light distribution panel in each of the light exposure apparatuses according to Embodiments 1 and 2 may be replaced by another light distribution panel depending on a current environment. For this reason, light distribution panels for use are not limited to the ones used in Embodiments 1 and 2.

In each of the light exposure apparatuses according to Embodiments 1 and 2, the intensity at the peak wavelength of the red light relative to the intensity at the peak wavelength of the blue light is obtained by adjusting the number of blue light emitting elements and the number of red light emitting elements. However, a relative intensity may be obtained by changing input electric power to be input to the red light source. In this case, for example, the relative intensity is obtained by means of a control circuit supplying electric power to each of the blue light source, red light source, etc.

In addition, a description is given of light emitting modules provided in the respective light exposure apparatuses according to Embodiments 1 and 2. The light emitting modules are configured by selectively including blue light emitting elements, red light emitting elements, white light emitting elements, and green light emitting elements. FIG. 9 is a diagram indicating the numbers of blue, red, white, and green light sources of the light exposure apparatus and chromaticity coordinates. FIG. 9 illustrates the relationships between the number of blue light emitting elements, the number of red light emitting elements, the number of green light emitting elements, and the number of white light emitting elements all mounted on the board of the light emitting module and chromaticity of light that is emitted from light exposure apparatus 1. The white light emitting elements used here has a color temperature of 6500 K.

In Example 1, the light emitting module used includes: thirty-two blue light emitting elements arranged along the outer circumference; and sixteen blue light emitting elements, eight red light emitting elements, and eight green light emitting elements all arranged along the inner circumference. In this case, the color coordinates in a chromaticity diagram are represented according to x=0.19 and y=0.11. In this case, reddish white light is emitted from the light exposure apparatus.

In Example 2, a light emitting module used includes: thirty-two blue light emitting elements arranged along the outer circumference; and eight blue light emitting elements, sixteen red light emitting elements, and eight green light emitting elements all arranged along the inner circumference. In this case, the color coordinates in a chromaticity diagram are represented according to x=0.25 and y=0.14. In this case, light that is closer to red than the light in Example 1 is emitted from the light exposure apparatus.

In Example 3, a light emitting module used includes: thirty-two blue light emitting elements arranged along the outer circumference; and twenty-four red light emitting elements, and eight green light emitting elements all arranged along the inner circumference. In this case, the color coordinates in a chromaticity diagram are represented according to x=0.31 and y=0.17. In this case, light that is closer to red than the light in Example 2 is emitted from the light exposure apparatus.

In Example 4, the light emitting module used includes: thirty-two white light emitting elements arranged along the outer circumference; and twelve blue light emitting elements, eight red light emitting elements, eight green light emitting elements, and four white light emitting elements all arranged along the inner circumference. In this case, the color coordinates in a chromaticity diagram are represented according to x=0.31 and y=0.15. In this case, white light is emitted from the light exposure apparatus.

In Example 5, the light emitting module used includes: thirty-two blue light emitting elements arranged along the outer circumference; and eight blue light emitting elements, eight red light emitting elements, eight green light emitting elements, and eight white light emitting elements all arranged along the inner circumference. In this case, the color coordinates in a chromaticity diagram are represented according to x=0.21 and y=0.15. In this case, bluish white light is emitted from the light exposure apparatus.

In Example 6, the light emitting module used includes: thirty-two blue light emitting elements arranged along the outer circumference; and eight red light emitting elements, eight green light emitting elements, and sixteen white light emitting elements all arranged along the inner circumference. In this case, the color coordinates in a chromaticity diagram are represented according to x=0.24 and y=0.19. In this case, light that is closer to blue than the light in Example 5 is emitted from the light exposure apparatus.

The face of the user looks too flushed in Example 3 and looks too pale in Example 5. For this reason, light emitting modules used in Examples 1, 2, 4, and 5 are suitable for use in the light exposure apparatuses in Embodiments 1 and 2.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A light exposure apparatus which emits emission light that activates a body of a user, the light exposure apparatus comprising:
   a blue light source which emits blue light; and
   a red light source which emits red light;
   wherein the emission light includes the blue light and the red light,
   the blue light has a peak wavelength in a wavelength range from 445 nm to 500 nm,
   the red light has a peak wavelength in a wavelength range from 600 nm to 680 nm,
   an intensity of the emission light is strongest at the peak wavelength of the blue light in a spectrum of the emission light,
   the intensity of the emission light is second strongest at the peak wavelength of the red light in the spectrum, and
   the intensity of the emission light at the peak wavelength of the red light is from 0.1 to 0.5 of the intensity at the peak wavelength of the blue light.

2. The light exposure apparatus according to claim 1, further comprising:
   a white light source which emits white light,
   wherein the emission light further includes the white light, and
   a minimum intensity of the emission light in a wavelength range from 550 nm to 600 nm in the spectrum is 0.03 or higher of the intensity at the peak wavelength of the blue light.

3. The light exposure apparatus according to claim 1,
   wherein the blue light source includes a plurality of blue light emitting elements, and
   the red light source includes a plurality of red light emitting elements,
   the light exposure apparatus further comprising:
   a light emitting module having a board which has a ring shape and on which the blue light source and the red light source are mounted;
   a case having an inner surface that reflects the emission light and a first opening portion through which the emission light reflected by the inner surface exits, the inner surface being approximately hemispherical; and
   a frame body attached to the first opening portion and having a second opening portion through which the reflected light passes,
   the light emitting module is oriented in the frame body to emit the emission light toward the inner surface of the case.

4. The light exposure apparatus according to claim 3, further comprising:
   a light distribution panel which covers the second opening portion, and passes through and distributes the emission light.

5. The light exposure apparatus according to claim 4,
   wherein the light distribution panel when disposed at the second opening portion has a property of reducing, by 30% or higher, brightness of light rays oriented at angles from 34 degrees to 40 degrees with respect to an optical axis of the light exposure apparatus, compared to when no light distribution panel is disposed at the second opening portion.

6. The light exposure apparatus according to claim 3,
   wherein the plurality of blue light emitting elements and the plurality of red light emitting elements are arranged annularly along the ring shape of the board,
   the plurality of blue light emitting elements are arranged along an outer circumference of the board, and
   the plurality of red light emitting elements are arranged along an inner circumference of the board.

7. The light exposure apparatus according to claim 6,
   wherein the plurality of blue light emitting elements are arranged in addition to the plurality of red light emitting elements such that the plurality of blue light emitting elements and the plurality of red light emitting elements are alternately arranged along the inner circumference of the board in units of a predetermined number of light emitting elements.

8. The light exposure apparatus according to claim 2,
   wherein the blue light source includes a plurality of blue light emitting elements,
   the red light source includes a plurality of red light emitting elements, and
   the white light source includes a plurality of white light emitting elements,
   the light exposure apparatus further comprising:
   a light emitting module having a board which has a ring shape and on which the blue light source, the red light source, and the white light source are mounted;
   a case having an inner surface that reflects the emission light and a first opening portion through which the emission light reflected by the inner surface exits, the inner surface being approximately hemispherical; and a frame body attached to the first opening portion and having a second opening portion through which the reflected light passes, the light emitting module is oriented in the frame body to emit the emission light toward the inner surface of the case.

9. The light exposure apparatus according to claim 8, wherein the plurality of blue light emitting elements, the plurality of red light emitting elements, and the plurality of white light emitting elements are arranged annularly along the ring shape of the board, the plurality of blue light emitting elements are arranged along an outer circumference of the board, the plurality of red light emitting elements are arranged along an inner circumference of the board, and the plurality of white light emitting elements are arranged along the inner circumference of the board.

10. The light exposure apparatus according to claim 1, wherein the intensity at the peak wavelength of the red light is from 0.2 to 0.3 of the intensity at the peak wavelength of the blue light.

* * * * *